(12) United States Patent
Rogers

(10) Patent No.: US 10,889,810 B2
(45) Date of Patent: Jan. 12, 2021

(54) METHODS AND KITS

(71) Applicant: Arcis Biotechnology Holdings Limited, Warrington (GB)

(72) Inventor: Jan Rogers, Chester (GB)

(73) Assignee: Arcis Biotechnology Holdings Limited, Daresbury (GB)

(*) Notice: Subject to any disclaimer, the term of this patent is extended or adjusted under 35 U.S.C. 154(b) by 0 days.

(21) Appl. No.: 16/511,333

(22) Filed: Jul. 15, 2019

(65) Prior Publication Data

US 2019/0338275 A1 Nov. 7, 2019

Related U.S. Application Data

(62) Division of application No. 15/515,437, filed as application No. PCT/GB2015/052863 on Sep. 30, 2015, now Pat. No. 10,711,264.

(30) Foreign Application Priority Data

Oct. 1, 2014 (GB) .................................. 1417372.8

(51) Int. Cl.
  *C12Q 1/68* (2018.01)
  *C12N 15/10* (2006.01)
  *C12Q 1/689* (2018.01)
  *C12Q 1/6893* (2018.01)
  *C12Q 1/6806* (2018.01)

(52) U.S. Cl.
  CPC ..... *C12N 15/1003* (2013.01); *C12N 15/1006* (2013.01); *C12Q 1/6806* (2013.01); *C12Q 1/689* (2013.01); *C12Q 1/6893* (2013.01); *C12Q 2600/158* (2013.01)

(58) Field of Classification Search
  CPC .......................... C12N 15/1003; C12Q 1/6806
  See application file for complete search history.

(56) References Cited

U.S. PATENT DOCUMENTS

2013/0157265 A1 6/2013 Mingorance Cruz et al.

FOREIGN PATENT DOCUMENTS

| CN | 102220419 A | | 10/2011 |
|---|---|---|---|
| KR | 2013/0071168 A | | 6/2013 |
| WO | WO-2005/094421 A2 | | 10/2005 |
| WO | WO-2008/011715 A1 | | 1/2008 |
| WO | WO-2010/080616 A1 | | 7/2010 |
| WO | WO-2011/133433 A2 | | 10/2011 |
| WO | WO-2012/160386 A1 | | 11/2012 |
| WO | WO-2013-175188 A1 | | 11/2013 |
| WO | WO-2013175188 A1 | * | 11/2013 |
| WO | WO-2014/122486 A1 | | 8/2014 |
| WO | WO-2014/155078 A1 | | 10/2014 |

OTHER PUBLICATIONS

Jing et al. (colloid Polym. Sci 282:1089-1096) (Year: 2004).*
Gibson et al. (Appl Environ Microbiol, 78(9):3037-3044) (Year: 2012).*
Rougemont et al. (Journal of Clinical Microbiology, 42(12):5636-5643) (Year: 2004).*
Baldwin et al., "Metagenomic Assay for Identification of Microbial Pathogens in Tumor Tissues", MBIO, vol. 5(5): e01714-14, Sep. 16, 2014.
Bessetti et al., "An Introduction to PCR Inhibitors", Promega (Internet Citation), Mar. 2007.
Farell et al., "Bovine serum albumin further enhances the effects of organic solvents on increased yield of polymerase chain reaction of GC-rich templates", BMC Research Notes, vol.5(1): 257, May 24, 2012.
Mollet et al., "RPOB Sequence Analysis as a Novel basis for Bacterial Identification", Molecular Microbiology, vol. 26(5): 1005-1011, Jan. 1, 1997.
Rothman et al., "Use of Quantitative Broad-based Polymerase Chain Reaction for Detection and Identification of Common Bacterial Pathogens in Cerebrospinal Fluid", Academic Emergency Medicine, vol. 17(7): 741-747, Jul. 1, 2010.
Rougemont et al., "Detection of four Plasmodium species in blood from humans by 18S rRNA gene subunit-based and species-specific real-time PCR assays", Journal of Clinical Microbiology, vol. 42(12): 5636-5643, Dec. 1, 2004.
Zucol et al., "Real-time Quantitative Broad-Range PCR Assay for Detection of the 16S rRNA Gene Followed by Sequencing for Species Identification", Journal of Clinical Microbiology, vol. 44(8): 2750-2759, Aug. 1, 2006.
Jing et al., "Phase behavior of DNA in the presence of cetyltrimethylammonium bromide/alkyl polyglucoside surfactant mixture", Colloid Polym Scie, vol. 282:1089-1096, Jan. 2004.
Gibson et al., "Removal and Transfer of Viruses on Food Contact Surfaces by Cleaning Cloths", Appl Environ Microbiol, vol. 78(9):3037-3044, Feb. 2012.
International Search Report issued on International Patent Application No. PCT/GB2015/052863, dated Mar. 29, 2016.
Non-Final Office Action, dated Sep. 10, 2019, issued on U.S. Appl. No. 15/515,437.
Non-Final Office Action, dated Mar. 27, 2019, issued on U.S. Appl. No. 15/515,437 and Response.

\* cited by examiner

*Primary Examiner* — Jezia Riley
(74) *Attorney, Agent, or Firm* — Howson & Howson LLP; Francis J. Coffey

(57) ABSTRACT

A method of detection and identification of one or more microorganism/s in a biological sample comprising the following steps:
  (a) extracting DNA from the microorganism/s; and
  (b) amplifying the extracted DNA and indicating the level of extracted DNA in a quantitative PCR;

wherein the quantitative PCR is performed using the primer pair of SEQ ID NO. 1 and 2 together with the probe of SEQ ID NO. 7, and/or the primer pair of SEQ ID NO. 3 and 4 together with the probe of SEQ ID NO. 8.

10 Claims, 2 Drawing Sheets

Specification includes a Sequence Listing.

SEQUENCE LISTING

<160> NUMBER OF SEQ ID NOS: 9

<210> SEQ ID NO 1
<211> LENGTH: 24
<212> TYPE: DNA
<213> ORGANISM: Artificial Sequence
<220> FEATURE:
<223> OTHER INFORMATION: Protozoan Forward Primer

<400> SEQUENCE: 1
gttaagggag tgaagacgat caga          24

<210> SEQ ID NO 2
<211> LENGTH: 26
<212> TYPE: DNA
<213> ORGANISM: Artificial Sequence
<220> FEATURE:
<223> OTHER INFORMATION: Protozoan Reverse Primer

<400> SEQUENCE: 2
aacccaaaga ctttgatttc tcataa          26

<210> SEQ ID NO 3
<211> LENGTH: 19
<212> TYPE: DNA
<213> ORGANISM: Artificial Sequence
<220> FEATURE:
<223> OTHER INFORMATION: Bacterial Forward Primer

<400> SEQUENCE: 3
ggaactggtg ccggaacgc          19

<210> SEQ ID NO 4
<211> LENGTH: 19
<212> TYPE: DNA
<213> ORGANISM: Artificial Sequence
<220> FEATURE:
<223> OTHER INFORMATION: Bacterial Reverse Primer

<400> SEQUENCE: 4
gacttcgatc agtttgacg          19

<210> SEQ ID NO 5
<211> LENGTH: 19
<212> TYPE: DNA
<213> ORGANISM: Artificial Sequence
<220> FEATURE:
<223> OTHER INFORMATION: Control Forward Primer

<400> SEQUENCE: 5
agatttggac ctgcgagcg          19

<210> SEQ ID NO 6
<211> LENGTH: 20
<212> TYPE: DNA
<213> ORGANISM: Artificial Sequence

```
<220> FEATURE:
<223> OTHER INFORMATION: Control Reverse Primer

<400> SEQUENCE: 6
gagcggctgt ctccacaagt                                              20

<210> SEQ ID NO 7
<211> LENGTH: 36
<212> TYPE: DNA
<213> ORGANISM: Artificial Sequence
<220> FEATURE:
<223> OTHER INFORMATION: Plasmodium sp Probe with 5'-FAM and 3'-TAMRA

<400> SEQUENCE: 7
accgtcgtaa tcttaaccat aaactatgcc gactag                            36

<210> SEQ ID NO 8
<211> LENGTH: 23
<212> TYPE: DNA
<213> ORGANISM: Artificial Sequence
<220> FEATURE:
<223> OTHER INFORMATION: E.coli Probe with 5'-FAM and 3'-TAMRA

<400> SEQUENCE: 8
cgtatcactg cgcgccacat tcg                                          23

<210> SEQ ID NO 9
<211> LENGTH: 23
<212> TYPE: DNA
<213> ORGANISM: Artificial Sequence
<220> FEATURE:
<223> OTHER INFORMATION: Human Probe with 5'-FAM/VIC and 3'-BHQ1

<400> SEQUENCE: 9
ttctgacctg aaggctctgc gcg                                          23
```

METHODS AND KITS

This application is a divisional of U.S. patent application Ser. No. 15/515,437, filed Mar. 29, 2017, which is a US National Stage entry of PCT/GB2015/052863, filed Sep. 30, 2015, which claims the benefit of GB application no. 1417372.8, filed Oct. 1, 2014. Each of these applications is incorporated by reference in its entirety.

The present invention relates to methods and kits for the detection of microorganism DNA from biological samples such as blood. More specifically the invention relates to methods and kits for the release of such DNA from biological samples and the detection thereof by the use of quantitative PCR.

Many clinical infections contained within the body, especially those diseases arising in bodily fluids such as blood or saliva, require quick detection before the condition of the subject deteriorates. In the case of blood bourne diseases like septicaemia and malaria, the infection can be severe and affect all organs of the body in a matter of days. This is well before the standard culturing and testing methods can identify what the source of the illness is, and requires extensive laboratory facilities which are not easily available in many parts of the world where such diseases are most prevalent. Furthermore such methods are labour intensive and require trained pathologists to implement, and cannot identify more than one pathogen at once.

More recently, genetic technologies for detection and diagnosis of such diseases have been developed which use the DNA or RNA extracted from a sample of blood, saliva etc. in a PCR method with subsequent sequencing or restriction fragment analysis to identify the relevant pathogens causing the disease. These methods rely on a series of steps to obtain the DNA and/or RNA from the sample including lysis and several rounds of purification, then several steps to conduct the PCR including mixing the obtained DNA/RNA with specific probes, primers and a PCR master mix, followed by a defined temperature schedule to replicate the DNA/RNA. Typically several different primers/probes are used that are specific to the pathogens to be detected, and typically each different pathogen must be detected in a separate assay.

The simultaneous detection of several pathogens in one biological sample has been reported. One such method is accomplished by using universal primers common to several or many pathogenic microorganisms, these primers typically bind highly conserved regions of genetic code such as that of the 16S or 32S ribosomal RNA. Other methods of detecting several different pathogens include the use of multiplex PCR whereby multiple pairs of primers are used in the same amplification reaction. However, although these methods are quicker and have wider general use than the standard PCR methods of the past, they are prone to false positives and negatives as the different primers require different annealing temperatures and the methods do not account for different amounts of pathogen DNA present in the sample. Furthermore, the PCR is often not conclusive and further diagnostics are required to identify the pathogenic organisms, such as pyrosequencing.

US2013/0157265 describes a process of identifying bacteria in a pre-prepared biological sample by pyrosequencing of three regions of conserved ribosomal RNA using three pairs of primers in successive PCR reactions and subsequently identifying the bacteria using sequence comparison software. Although this method works to identify more than one pathogen per sample, and can be provided in a kit of self-contained PCR reactions that are ready to use, the method cannot identify anything other than bacteria, and the three conserved regions of genome used to identify the pathogen are large sections of ribosomal RNA. The sequencing of which takes a long time and is expensive.

Accordingly, in the prior methods, the entire process of diagnostics from obtaining the sample to the end sequencing results still requires several technically involved steps, each with separate equipment, and each introducing a possible source of error. Firstly, the genetic material required for the identification of pathogens by PCR must be very pure and this has resulted in complex methods of purification of DNA/RNA from biological samples. Secondly, the industrially feasible PCR reactions of the prior art are still limited to the identification of either separate pathogens in each assay or bacteria alone, and still require a separate sequencing process which itself requires long fragments of genetic material to be sequenced.

It is an aim of one or more aspects of the present invention to address one or more of the aforementioned problems of the prior art.

According to a first aspect of the present invention, there is provided a method of detection and identification of one or more microorganism/s in a biological sample comprising the following steps:
 (a) extracting DNA from the microorganism/s by contacting the microorganism/s with an extraction solution comprising a quaternary ammonium compound including a silicon containing functional group; and
 (b) amplifying the extracted DNA and indicating the level of extracted DNA in a quantitative PCR.

According to a second aspect of the present invention, there is provided a method of detection and identification of one or more microorganism/s in a biological sample comprising the following steps:
 (a) extracting DNA from the microorganism/s; and
 (b) amplifying the extracted DNA and indicating the level of extracted DNA in a quantitative PCR;
wherein the quantitative PCR is performed using the primer pair of SEQ ID NO. 1 and 2 together with the probe of SEQ ID NO. 7, and/or the primer pair of SEQ ID NO. 3 and 4 together with the probe of SEQ ID NO. 8.

Suitably the first and second aspects of the present invention together provide a method of detection and identification of one or more microorganism/s in a biological sample comprising the following steps:
 (a) extracting DNA from the microorganism/s by contacting the microorganism/s with an extraction solution comprising a quaternary ammonium compound including a silicon containing functional group; and
 (b) amplifying the extracted DNA and indicating the level of extracted DNA in a quantitative PCR;
wherein the quantitative PCR is performed using the primer pair of SEQ ID NO. 1 and 2 together with the probe of SEQ ID NO. 7, and/or the primer pair of SEQ ID NO. 3 and 4 together with the probe of SEQ ID NO. 8.

Preferred features of the first and second are set out below. Any preferred feature may be combined with any of the aspects in any combination.

Advantageously, the method of the present invention provides a two-step simple process by which microorganism/s can be identified directly from the biological sample without the need for separate purification steps and without the need for a separate sequencing step to identify the microorganism/s. Furthermore, the primers used in the present invention have surprisingly been found to work with both eukaryotic and prokaryotic microorganisms, meaning that the method is universally applicable to all types of microorganism that may be contained in a sample in a single polymerase chain reaction.

The specific probes identified herein are advantageously able to work with the primers to identify specifically *E. coli* and *Plasmodioum* sp. in a biological sample within the single PCR step itself. *E. coli* and *Plasmodium* sp. are the major cause of blood-bourne illnesses, especially the most common diseases of septicaemia and malaria. Accordingly, the present method allows quicker and cheaper identification of these pathogens in a sample than traditional methods; this will reduce deaths from these diseases and make such testing more accessible to poorer areas of the world where such diseases are more common.

Preferably step (a) comprises extracting DNA from the microorganism/s by contacting the biological sample with an extraction solution.

The biological sample may be obtained from a bodily fluid of a human or animal, for example include blood and blood components, mucus, saliva, urine, vomit, faeces, sweat, semen, vaginal secretion, tears, pus, sputum or pleural fluid.

Preferably the extraction solution comprises a quaternary ammonium compound including a silicon containing functional group.

By silicon-containing group we mean to refer to any group including a silicon atom. Preferred silicon-containing functional groups are those which include a silicon atom covalently bonded via four single bonds to four organic moieties. The silicon atom may be directly bonded to oxygen and/or carbon atoms.

Preferably step (a) involves contacting the sample with an extraction solution comprising a compound of general formula (I):

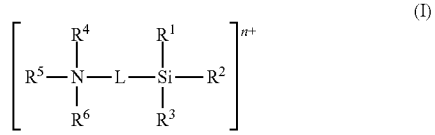
(I)

or a derivative salt thereof wherein L is a linking group; each of $R^1$, $R^2$, $R^3$, $R^4$, $R^5$ and $R^6$ is independently selected from H or an optionally substituted alkyl, alkenyl, aryl or alkoxy group; and n is 0 or 1.

It will be appreciated that in embodiments in which n is 1, the species shown in formula (I) is a cationic species.

In such embodiments the species of formula (I) will be present as an adduct or salt including a suitable counterion. However for ease of reference, in this document we may make general reference to compounds of formula (I) and any such reference includes where appropriate any counterion which must be present.

Any suitable counterion may be used. Monovalent counterions are preferred. Suitable counterions include halides and oxyhalo ions for example chloride, bromide, bromite, chlorite, hypochlorite, chlorate, bromate and iodate. In a most preferred embodiment the counterion is a chloride ion.

In this specification any optionally substituted alkyl, alkenyl, aryl or alkoxy group may be optionally substituted with one or more substituents selected from halo, hydroxy, nitro, mercapto, amino, alkyl, alkoxy, aryl, sulfo and sulfoxy.

Preferred substituents which may be present in the alkyl, alkenyl, aryl or alkoxy groups defined herein are halogens, in particular fluorine. In particular each of $R^1$, $R^2$, $R^3$, $R^4$, $R^5$ or $R^6$ may comprise fluoroalkyl or fluoroalkoxy groups which may comprise one or more fluorine atoms.

Each of $R^1$, $R^2$ and $R^3$ is independently selected from an optionally substituted alkyl, alkenyl, aryl or alkoxy group. Preferably at least one of $R^1$, $R^2$ and $R^3$ is an optionally substituted alkoxy group. More preferably each of $R^1$, $R^2$ and $R^3$ is an optionally substituted alkoxy group, most preferably each is an unsubstituted alkoxy group. The alkyl group of the alkoxy group may be straight chained or branched. Preferably each of $R^1$, $R^2$ and $R^3$ is an alkoxy group having from 1 to 20 carbon atoms, preferably from 1 to 16 carbon atoms, more preferably from 1 to 12 carbon atoms, preferably from 1 to 8 carbon atoms, suitably from 1 to 6 carbon atoms, more preferably from 1 to 4 carbon atoms.

In preferred embodiments each of $R^1$, $R^2$ and $R^3$ is independently selected from methoxy, ethoxy, propoxy, butoxy and isomers thereof. Most preferably each of $R^1$, $R^2$ and $R^3$ is selected from methoxy, ethoxy and isopropoxy. Preferably each of $R^1$, $R^2$ and $R^3$ is selected from methoxy and ethoxy. Most preferably each of $R^1$, $R^2$ and $R^3$ is methoxy. Preferably each of $R^1$, $R^2$ and $R^3$ is the same.

$R^4$ and $R^6$ is preferably an alkyl group having from 1 to 8 carbon atoms, most preferably 1 to 6 carbon atoms, more preferably 1 to 4 carbon atoms. $R^4$ and $R^6$ may suitably be selected from methyl, ethyl, propyl, butyl and isomers thereof. Preferably $R^4$ and $R^6$ is methyl or ethyl. Most preferably $R^4$ and $R^6$ is methyl.

Preferably $R^5$ is an alkyl group having from 8 to 30 carbon atoms, for example from 10 to 26 carbon atoms, suitably from 12 to 24 carbon atoms, preferably from 14 to 22 carbon atoms, suitably from 16 to 20 carbon atoms, for example 17 to 19 carbon atoms, suitably 18 carbon atoms.

L is a linking group. It may suitably be a bond or an optionally substituted alkylene, alkenylene or arylene group. Preferably L is an optionally substituted alkenylene group. It may be substituted along the chain or within the chain. For example L may be an ether linking moiety, i.e. a group of formula $O(CH_2)_n$ in which n is 1 to 12, preferably 1 to 6.

Preferably L is an unsubstituted alkylene group, more preferably an alkylene group having 1 to 12 carbon atoms, preferably 1 to 10 carbon atoms, suitably 1 to 8 carbon atoms, for example 2 to 8 carbon atoms, more preferably 2 to 6 carbon atoms, suitably 2 to 5 carbon atoms for example 2 to 4 carbon atoms. In especially preferred embodiments L is a propylene group.

In especially preferred embodiments of the compound of formula (I), $R^1$, $R^2$ and $R^3$ are each $C_1$ to $C_4$ alkoxy, L is a $C_2$ to $C_5$ alkylene group, $R^4$ and $R^6$ are each $C_1$ to $C_4$ alkyl groups and $R^5$ is a $C_{12}$ to $C_{24}$ alkyl group.

Most preferably the compound of formula (I) is the compound shown in formula (II). This compound is commercially available as a solution in methanol.

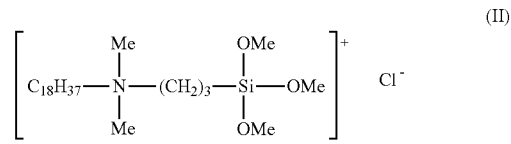
(II)

The extraction solution contacted with the sample in the method of the first aspect may be provided in any suitable form. It may consist essentially of the quaternary ammonium compound having a silicon-containing functional group or it may comprise one or more further components.

Suitably the extraction solution includes one or more solvents. Preferred solvents are water and water miscible solvents. In embodiments in which the quaternary ammonium compound is obtained commercially as a solution in methanol, much of the methanol is suitably removed prior to use of the extraction solution in the method of the present invention.

Preferably the extraction solution is aqueous. In especially preferred embodiments water comprises at least 90 wt %, more preferably at least 95 wt % or at least 99 wt % of cell solvents present in the extraction solution. In one preferred embodiment the extraction solution is freeze dried. In such embodiments an aqueous mixture may be provided upon contact with an aqueous composition comprising the biological sample. Freeze-dried extraction solutions may be advantageous for storage and distribution.

The extraction solution contacted with the biological sample in the method of the first aspect preferably comprises at least 0.001 wt % of a quaternary ammonium compound including a silicon-containing functional group, preferably at least 0.01 wt %, more preferably at least 0.04 wt %, and more preferably at least 0.06 wt %.

The quaternary ammonium compound including a silicon-containing functional group preferably comprises up to 10 wt % of the composition contacted with the cell or capsid, suitably up to 5 wt %, preferably up to 1 wt %, preferably up to 0.5 wt %, more preferably up to 0.2 wt %, and more preferably up to 0.1 wt %.

The extraction solution used in the method of the present invention may consist essentially of the compound of general formula (I) or may further include other components.

In addition to solvents mentioned above, further components may include one or more of a solubilising agent, a buffer, and a PCR promoting agent.

Preferably the extraction solution further comprises a solubilising agent.

Suitable solubilising agents include any compound that improves the solubility, especially the solubility in water, of the quaternary ammonium compound including a silicon-containing functional group.

Examples of suitable solubilising agents include non-ionic surfactants. Non-ionic surfactants may have a hydrophilic portion, suitably an alkoxylate moiety or a sugar moiety. Suitable non-ionic surfactants include alcohol ethoxylates and fatty alcohol polyglycosides. Suitably the hydrophilic-lipophilic balance (HLB) value of a non-ionic surfactant used in the present invention is at least 7, and preferably at least 10. Especially suitable non-ionic surfactants may have an HLB value falling in the range 10-16, preferably 10-14. For the purposes of these definitions HLB value is determined by the classical method of Griffin (Griffin W C: "Calculation of HLB Values of Non-Ionic Surfactants," Journal of the Society of Cosmetic Chemists 5 (1954): 249).

Suitable solubilising agents for use herein include hydrocarbyl saccharide compounds. By hydrocarbyl-saccharide compound we mean to refer to a compound including a hydrocarbyl group and a saccharide moiety.

The hydrocarbyl group may be bound to the saccharide moiety via a carbon-carbon bond or via a carbon-oxygen bond. Preferably it is bound to the saccharide moiety via a carbon-oxygen bond, for example via an ester linkage or an ether linkage. Most preferably it is bound to the oligosaccharide moiety via an ether linkage. Thus in preferred embodiments the solubilising agent is a hydrocarbyl ether of a saccharide moiety.

The hydrocarbyl-saccharide compound may include one or more hydrocarbyl groups. Preferably it comprises one hydrocarbyl group. The hydrocarbyl group may be an optionally substituted alkyl, alkenyl or alkynylene group. Most preferably it is an optionally substituted alkyl group. Suitable substituents include halo, hydroxy, nitro, mercapto, amino, alkyl, alkoxy, aryl, sulfo and sulfoxy. Any substitution may be within the chain or along it, for example the chain may include an ether linkage.

Preferably the hydrocarbyl group is an unsubstituted alkyl group. It may be straight chained or may be branched. Most preferably it is straight chained. Especially preferred hydrocarbyl groups are alkyl groups having from 1 to 30 carbon atoms, preferably 2 to 24 carbon atoms, more preferably from 4 to 20 carbon atoms, suitably from 4 to 16 carbon atoms, preferably from 6 to 14 carbon atoms, for example from 6 to 12 carbon atoms and most preferably from 8 to 10 carbon atoms. Preferred are straight chained alkyl groups having from 6 to 12 carbon atoms.

The saccharide moiety of the hydrocarbyl oligosaccharide species may include from 1 to 10 monosaccharide species. Thus it may be a monosaccharide unit, a disaccharide unit or an oligosaccharide unit. Preferably the saccharide moiety comprises from 2 to 8, suitably from 2 to 6, preferably from 2 to 5, for example 3 or 4 monosaccharide units. Any suitable monosaccharide unit may be included. Preferred saccharides include allose, altrose, glucose, mannose, gulose, idose, galactose and talose.

Mixtures of two or more monosaccharides may be present in the saccharide moiety. Preferably the saccharide moiety comprises glucose. More preferably all of the monosaccharide units present in the saccharide moiety are glucose.

In a preferred embodiment the solubilising agent is an alkyl polyglucoside (APG), preferably a monoalkyl-polyglucoside. Suitably the solubilising agent is a compound of general formula (III):

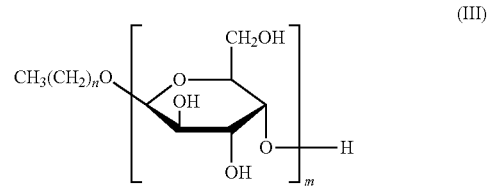

(III)

wherein n is from 5 to 12, preferably from 6 to 10, more preferably from 7 to 9 and m is from 1 to 6, preferably from 2 to 5, more preferably 3 or 4.

The solubilising agent is suitably present in the extraction solution contacted with the biological sample in an amount of at least 0.001 wt %, preferably at least 0.01 wt %, more preferably at least 0.04 wt %, and more preferably at least 0.06 wt %.

The solubilising agent may be present in the extraction solution contacted with the biological sample in an amount of up to 10 wt % of the composition, suitably up to 5 wt %, preferably up to 1 wt %, preferably up to 0.5 wt %, more preferably up to 0.2 wt %, and more preferably up to 0.1 wt %.

The weight ratio of the quaternary ammonium compound including a silicon-containing functional component to the solubilising agent is preferably from 1:10 to 10:1, preferably from 1:5 to 5:1, preferably from 1:3 to 3:1, suitably from 1:2.5 to 2.5:1.

In some embodiments the weight ratio of the quaternary ammonium compound including a silicon-containing functional component to the solubilising.agent is from 1:2 to 2:1, preferably from 1:1.5 to 1.5:1, and more preferably from 1:1.2 to 1.2:1.

In some embodiments the weight ratio of the quaternary ammonium compound including a silicon-containing functional component to the solubilising.agent is from 4:1 to 1:1, preferably from 3:1 to 1.5:1, and more preferably from 2.2:1 to 1.8:1.

The extraction solution may comprise a buffer. Any suitable buffer can be used. Preferred buffers are biologically acceptable buffers. Examples of suitable buffers include but are not limited to N-(2-acetamido)-aminoethanesulfonic acid, acetate, N-(2-acetamido)-iminodiacetic acid, 2-aminoethanesulfonic acid, ammonia, 2-amino-2-methyl-1-propanol, 2-amino-2-methyl-1,3-propanediol, N-(1,1-dimethyl-2-hydroxyethyl)-3-amino-2-hydroxypropanesulfonic acid, N,N-bis-(2-hydroxyethyl)-2-aminoethanesulfonic acid, sodium hydrogen carbonate, N,N'-bis(2-hydroxyethyl)-glycine, [bis-(2-hydroxyethyl)-imino]-tris-(hydroxymethylmethane), 1,3-bis[tris(hydroxymethyl)-methylamino]propane, boric acid, dimethylarsinic acid, 3-(cyclohexylamino)-propanesulfonic acid, 3-(cyclohexylamino)-2-hydroxyl-1-propanesulfonic acid, sodium carbonate, cyclohexylaminoethanesulfonic acid, citrate, 3-[N-bis(hydroxylethyl)amino]-2-hydroxypropanesulfonic acid, formate, glycine, glycylglycine, N-(2-hydroxyethyl)-piperazine-N'-ethanesulfonic acid, N-(2-hydroxyethyl)-piperazine-N'-3-propanesulfonic acid, N-(2-hydroxyethyl)-piperazine-N'-2-hydroxypropanesulfonic acid, imidazole, malate, maleate, 2-(N-morpholino)-ethanesulfonic acid, 3-(N-morpholino)-propanesulfonic acid, 3-(N-morpholino)-2-hydroxypropanesulfonic acid, phosphate, piperazine-NN-bis(2-ethanesulfonic acid), piperazine-N,N'-bis(2-hydroxypropanesulfonic acid), pyridine, succinate, 3-{[tris(hydroxymethyl)-methyl]-amino}-propanesulfonic acid, 3-[N-tris(hydroxymethyl)-methylamino]-2-hydroxypropanesulfonic acid, 2-ami noethanesulfonic acid, triethanolamine, 2-[tris(hydroxymethyl)-methylamino]-ethanesulfonic acid, N-[tris(hydroxymethyl)-methyl]-glycine, tris(hydroxymethyl)-aminomethane, One especially preferred buffer is tris(hydroxymethyl)-aminomethane (TRIS).

The extraction solution preferably has a pH of from 6.5 to 8.5, more preferably from 7 to 8.

The concentration of the buffer is suitably selected to maintain a desired pH.

In some embodiments the extraction solution contacted with the biological sample in the method of the first aspect includes a PCR promoting agent. A PCR promoting agent may increase the yield of the desired PCR product or decrease the production of undesired products. Examples of suitable PCR promoting agents will be known to the person skilled in the art and include betaines, DMSO, formamide, bovine serum albumin (BSA), gelatin, non-ionic detergents for example Tween®-20, NP-40, and Triton® X-100, ammonium ions, glycerol, polyethylene glycol, tetramethyl ammonium salts, and divalent metal ions. In preferred embodiments the PCR promoting agent comprises a divalent metal. Preferably the PCR promoting agent comprises $Mg^{2+}$ ions, preferably as a water salt. Most preferably the PCR promoting agent is magnesium chloride.

The PCR promoting agent is preferably present in the extraction solution in a concentration of at least 0.01 mmol, preferably at least 0.05 mmol, and more preferably at least 0.1 mmol, The PCR promoting agent may be present in the extraction solution in an amount of up to 5 mmol, suitably up to 1 mmol, preferably up to 0.5 mmol, and more preferably up to 0.3 mmol.

Optionally, step (a) may additionally or alternatively comprise extraction of RNA from the microorganism/s, preferably by the same method as described above. In such embodiments, preferably the method of the first aspect further comprises a step of converting the RNA into cDNA, suitably before step (b) of the method. Suitably the conversion of RNA into cDNA comprises the use of a DNA polymerase enzyme and a mixture of nucleotide bases to produce double stranded cDNA as is known in the art.

Preferably the microorganism/s are pathogenic microorganism/s, more preferably pathogenic prokaryotic and/or eukaryotic microorganism/s, still more preferably pathogenic bacteria or protozoa. Accordingly, the method of the first aspect may be considered a method for diagnosing a disease in a subject on the basis of identification of the relevant pathogenic microorganism/s from the biological sample acquired therefrom.

Preferably the pathogenic bacteria are selected from of the genera *Bacteroides, Bartonella, Bordetella, Borrelia, Brucella, Campylobacter, Chlamydia, Escherichia, Francisella, Haemophilus, Helicobacter, Klebsiella, Legionella, Leptospira, Moraxella, Neisseria, Pasteurella, Proteus, Pseudomonas, Salmonella, Shigella, Spirillum, Streptobacillus, Treponema, Vibro, Yersinia, Actinomyces, Bacillus, Clostridium, Corynebacterium, Listeria, Nocardia, Peptostreptococcus, Propionibacterium, Staphylococcus, Streptococcus*, or *Streptomyces*. Most preferably the pathogenic bacterium is *Escherichia coli*.

Preferably the pathogenic protozoa are selected from the genera *Acanthamoeba, Ancylostoma, Ascaradia, Babesia, Balamuthia, Balantidium, Brugia, Clonorchis, Cryptosporidium, Dicrocoelium, Dicytocaulus, Dientamoeba, Diphylobothrium, Dirofilaria, Echinococcus, Echinostoma, Entamoeba, Enterobius, Fasciola, Fascioloides, Giardia, Hymenolepsis, Isospora, Leishmania, Mesocestoides, Moniezia, Necator, Naegleria, Onchocerca, Opisthorchis, Paragonimus, Plasmodium, Rhabditida, Schistosoma, Spirurida, Strongyloides, Taenia, Trichomonas, Trichuris, Toxocara, Trypanosoma, Uncinaria* or *Wuchereria*. Most preferably the pathogenic protozoa is selected from *Plasmodium falciparum, Plasmodium vivax, Plasmodium ovale,* or *Plasmodium malariae*.

Preferably extraction of the DNA further comprises at least a first incubation of the sample. Preferably the first incubation takes place at room temperature, suitably between 15° C. and 30° C., more preferably 20° C. to 25° C., still more preferably 21° C. Preferably the first incubation takes place for around 5 to 15 minutes, more preferably 8 to 12 minutes, most preferably 10 minutes.

Preferably extraction of the DNA further comprises mixing of the sample. Preferably mixing is achieved by vortexing the sample. Preferably the sample is mixed a plurality of times over the first incubation period, more preferably three times. Preferably the mixing takes place for a period of 5-15 seconds, more preferably 8-12 seconds, most preferably 10 seconds each time.

Preferably the extraction of the DNA further comprises a second incubation of the sample. Preferably the second incubation takes place at around 85 to 105° C., more preferably 90 to 100° C., most preferably 95° C.

In some embodiments step (a) further comprises isolating the DNA from the sample, suitably after extraction thereof. Preferably the isolation comprises separating the biological sample into a lysate and a supernatant, wherein suitably the supernatant contains the DNA of the microorganism/s. Preferably separating the biological sample comprises centrifuging the sample such that insoluble material such as organelles, cell walls etc. are pelleted to the bottom. Preferably the centrifugation takes place at around 5000-20000 rpm, more preferably 8000-17000 rpm, still more preferably 10000-15000 rpm, most preferably 13000 rpm. Preferably the centrifugation takes place for around 5-15 minutes, more preferably 8-12 minutes, most preferably 10 minutes.

In some preferred embodiments of the method of the first aspect there is a step (a2) between step (a) and step (b) of contacting the material obtained in step (a) with a proteinaceous washing agent.

Suitably there are no purification steps between step (a) and step (a2) and the material obtained in step (a) is used directly in step (a2).

Preferred proteinaceous washing agents are anionic proteins.

Suitable proteinaceous washing agents include tryptone, gelatin, casein and bovine serum albumin (BSA). Preferred proteinaceous washing agents include bovine serum albumin and casein. An especially preferred washing agent is BSA. Acetylated bovine serum albumin (BSA) is particularly preferred.

Suitably the proteinaceous washing agent is present in the composition used in step (a2) in an amount from 0.01 to 50 wt %, preferably 0.1 to 10 wt %, suitably from 0.1 to 5 wt %, for example about 1 wt %.

Suitably the composition used in step (a2) of the method of the first aspect of the present invention is an aqueous composition. Suitably water comprises at least 90 wt % of all solvents present in the composition, preferably at least 95 wt % for example at least 99 wt % of all solvents present in the composition.

In one embodiment the composition may be freeze dried. In such an embodiment an aqueous mixture may be provided upon contact with the aqueous composition obtained in step (a).

In step (a2) of the method of the present invention suitably the composition obtained in step (a) is added to a composition containing the proteinaceous washing agent in a ratio of from 10:1 to 1:100, preferably from 5:1 to 1:50, suitably from 1:1 to 1:10.

It should be noted that the method of the present invention does not necessarily include using all of the mixture obtained in step (a) in step (a2). In many instances a portion of the composition obtained in step (a) is contacted with the composition comprising the proteinaceous washing agent in step (a2).

Suitably in step (a2) of the method of the present invention the mixture is briefly agitated at room temperature. It may be left for a period of 1 second to 24 hours, suitably 5 seconds to 1 hour, preferably 5 seconds to 30 minutes, preferably 10 seconds to 10 minutes, suitably from 30 seconds to 5 minutes, for example about 1 minute.

It has been surprisingly found that the mixture obtained in step (a2) of the present invention can be used directly in step (b).

It is highly advantageous that the method of the present invention provides a simple process in which DNA or RNA suitable for amplification can be obtained directly from whole blood.

Preferably step (b) comprises the addition of at least one reagent for performing the quantitative PCR. Suitably the at least one reagent is added to the extracted DNA of step (a), more preferably to the supernatant containing the extracted DNA.

Preferably the at least one reagent is selected from: DNA polymerase, buffer, dNTPs, or a source of Magnesium. More preferably step (b) comprises the addition of all three of these components, referred to as a PCR master mix. The master mix may suitably be sourced from any manufacturer, however preferably the Taqman® Master Mix from Applied Biosystems or the Promega M7502 mix is used.

Preferably the DNA Polymerase is a Taq DNA polymerase. Preferably the dNTPs include dATP, dGTP, dTTP, and dCTP in equal quantities. Preferably the source of Magnesium is Magnesium chloride. Preferably the buffer is any suitable buffer with a pH of 8.5

Preferably the PCR Master Mix is added to the extracted DNA in an amount of 5-20 µl, more preferably 7-17 µl, still more preferably 10-15 µl, most preferably 12.5 µl.

Suitably step (b) further comprises the addition of the primers and probes as required for the quantitative PCR amplification of step (b) of the method to the extracted DNA of step (a) of the method. Preferably the primer pairs are added in equal amounts to the extracted DNA of step (a) of the method, preferably each of the forward and reverse primers are added in an amount of between 0.1-0.9 µl, more preferably 0.2-0.7 µl, still more preferably 0.25-0.5 µl. Preferably the probes are added in an amount of between 0.2-2 µl, more preferably 0.3-1.75 µl, still more preferably 0.5-1.25 µl.

Preferably step (b) further comprises the addition of water to the extracted DNA of step (a) of the method. Preferably the water is deionised. Preferably the amount of water added is sufficient to make the reaction volume for the quantitative PCR in step (b) up to 20 µl.

Preferably step (b) further comprises amplifying and indicating the level of a control DNA together with the extracted DNA, the control DNA being definitively present within the biological sample. Preferably the control DNA is a human DNA when the biological sample is of human origin, or an animal DNA when the biological sample is of animal origins. More preferably the control DNA is a human DNA, preferably the control human DNA is of a housekeeping gene or genes that are substantially conserved in human DNA, more preferably the control human DNA is the RNAse-P gene.

Suitably therefore, a control primer pair and probe are added to the extracted DNA of step (a) together with the test primers of step (b) of the method. Preferably the control primer pair is that of SEQ ID NO. 5 and 6. and the probe is that of SEQ ID NO. 9.

Suitably the primer pairs and probes added at step (b) of the method are specific to the type of microorganism/s being identified. Suitably the primer pair of SEQ ID NO. 1 and 2 together with the probe of SEQ ID NO. 7 are for identifying protozoan DNA, more specifically for identifying *Plasmodium* DNA. Suitably the primer pair of SEQ ID NO. 3 and 4 together with the probe of SEQ ID NO. 8 are for identifying bacterial DNA, more specifically for identifying *Escherichia* DNA. Suitably, the relevant sequences are as follows:

```
Primer Protozoan Forward:
                                         (SEQ ID NO. 1)
5'-GTTAAGGGAGTGAAGACGATCAGA-3'

Primer Protozoan Reverse:
                                         (SEQ ID NO. 2)
5'AACCCAAAGACTTTGATTTCTCATAA-3'

Probe Plasmodium:
                                         (SEQ ID NO. 7)
5'-FAM-ACCGTCGTAATCTTAACCATAAACTATGCCGACTAG-
TAMRA-3'

Primer Bacterial Forward:
                                         (SEQ ID NO. 3)
EcoF 5'-GGAACTGGTGCCGGAACGC-3'

Primer Bacterial Reverse:
                                         (SEQ ID NO. 4)
5'-GACTTCGATCAGTTTGACG-3'

Probe E. coli:
                                         (SEQ ID NO. 8)
5'-FAM-CGTATCACTGCGCGCCACATTCG-TAMRA-3'

Control Primer Forward:
                                         (SEQ ID NO. 5)
5'-AGA TTTGGACCTGCGAGCG-3'

Control Primer Reverse:
                                         (SEQ ID NO. 6)
5'-GAGCGGCTGTCTCCACAAGT-3'

Probe Human:
                                         (SEQ ID NO. 9)
5'-FAM/VIC-TTCTGACCTGAAGGCTCTGCGCG-BHQ1-3'
```

Suitably the quantitative PCR of step (b) of the method takes place using standard procedures known in the art and using standard machinery known in the art. qPCR is described in Higuchi R et al. Kinetic PCR analysis: Real time Monitoring of DNA amplification reactions. Bio/Technology 1993; 11:1026-30.

Suitably the amplification of the extracted DNA of step (a) is conducted by a set program of heating cycles during quantitative PCR as is known in the art. The heating cycle may comprise any of the following stages: mix activation, initial denaturation, denaturation, annealing, extension, final extension, or cooling. Suitably the heating cycle comprises at least initial denaturation, denaturation, and annealing. Optionally, any of the stages may be repeated, alone or in combination with any other stage. Preferably the denaturation and annealing stages are repeated, more preferably these stages are repeated for between 25 and 55 cycles, more preferably for between 30 and 45 cycles.

Preferably mix activation takes place at about 40 C to 60° C., more preferably about 50° C. for between 1 to 3 minutes, more preferably 2 minutes.

Preferably initial denaturation takes place at between 90 C-100° C., more preferably between 94 C-95° C. for between 1-20 minutes, more preferably between 2 to 15 minutes, most preferably between 5-10 minutes.

Preferably denaturation takes place at between 90 C-100° C., more preferably between 94 C-95° C. for between 10 to 30 seconds, more preferably between 15-20 seconds.

Preferably annealing takes place at between 45 C-70° C., more preferably 50 C-65° C., most preferably between 54 C-60° C. for between 10-70 seconds, more preferably 20-60 seconds.

Preferably extension takes place at between 60 C-80° C., more preferably 65 C-75° C., most preferably at 72° C. for between 5-20 seconds, more preferably 10 seconds.

Preferably final extension takes place 60 C-80° C., more preferably 65 C-75° C., most preferably at 72° C. for between 1-10 minutes, more preferably 2-7 minutes, most preferably 5 minutes.

Preferably cooling takes place at between 2 C-20° C., more preferably 5 C-15° C., most preferably 10° C. for any length of time.

In one embodiment, the heating cycle comprises the following:

| | | |
|---|---|---|
| Mix activation | 50° C. 2 min | |
| Initial denaturation | 95° C. 10 min | |
| Denaturation | 95° C. 15 sec | |
| | | 45 cycles |
| Annealing | 60° C. 60 sec | |

Preferably this heating cycle is used when conducting quantitative PCR.

In another embodiment, the heating cycle comprises the following:

| | | |
|---|---|---|
| Initial denaturation | 94° C. 5 min | |
| Denaturation | 94° C. 20 sec | |
| Annealing | 54° C. 20 sec | 30 cycles |
| Extension | 72° C. 30 sec | |
| Final extension | 72° C. 5 min | |
| Cooling | 10° C. ∞ | |

Preferably this heating cycle is used when conducting any other type of PCR, for example end-point PCR.

Optionally, the method of the first aspect may further comprise a step of analysing the PCR products of step (b) by electrophoresis, preferably agarose gel electrophoresis. Methods of conducting such analyses are well known in the art.

Preferred embodiments of the present invention involve using the previously identified combinations of primer pairs and probes to identify the relevant microorganism/s. The use of the probe allows visualisation of the PCR products as they are produced during PCR in step (b) of the method. The probes act to bind to the PCR products they when they recognise the specific organism DNA they are complementary to, and as that PCR product is replicated during the PCR process, the probes increase in fluorescence. This fluorescence is visualised with the aid of graphical representation (as shown in FIGS. 1, 2, and 4) to indicate the detection of specific organism DNA within the sample undergoing PCR.

However it is also within the scope of the invention to use an alternative visualisation method.

Therefore, according to a third aspect of the present invention, there is provided a method of detection and identification of one or more microorganism/s in a biological sample comprising the following steps:
 (a) extracting DNA from the microorganism/s;
 (b) amplifying the extracted DNA in a PCR; and
 (c) visualising the PCR products of step (b);
wherein the PCR in step (b) is performed using the primer pair of SEQ ID NO. 1 and 2 and/or the primer pair of SEQ ID NO. 3 and 4.

By the term 'visualisation' as used herein, it is meant that the PCR products of step (b) are manipulated such that they can be detected and such that the microorganism source of the DNA contained in the PCR products can be identified directly from the PCR products themselves. Preferably the visualisation does not require sequencing of the DNA contained in the PCR products. Advantageously therefore, the identification of the PCR products is much quicker and simpler than prior art processes because the PCR products do not have to undergo a costly and time consuming further sequencing stage to identify the source of the DNA contained therein.

In one embodiment step (c) may involve visualisation using the primer pair of SEQ ID NO. 1 and 2 together with the probe of SEQ ID NO. 7, and/or the primer pair of SEQ ID NO. 3 and 4 together with the probe of SEQ ID NO. 8 as described hereinabove. In such an embodiment, step (b) involves using quantitative PCR such that the probes bind to the relevant PCR products as they are produced during the PCR. Advantageously, therefore the identification of the DNA contained in the PCR products is immediate from the PCR itself.

In a further embodiment step (c) may involve visualisation of the PCR products using electrophoresis, suitably gel electrophoresis, preferably agarose gel electrophoresis. Suitably, as is known in the art, the PCR products are mixed with an intercalating agent, such as for example ethidium bromide and suitably the mixture is injected into wells in the gel before the application of a current thereto. In such an embodiment, step (b) involves using any type of PCR to amplify the extracted DNA, but preferably end-point PCR. Advantageously therefore the identification of DNA contained in the PCR products is able to performed quickly after the PCR, and this embodiment further allows the method to be used with any type of PCR and without the requirement for probes, Suitably in such an embodiment, the requirements for conducting the PCR are the same as set out above in relation to quantitative PCR, specifically the components required for the PCR of step (b) and the heating cycle specifications.

Further preferred features of the method of the third aspect are set out hereinabove in relation to the second and third aspects.

According to a fourth aspect of the present invention, there is provided a kit for the detection and identification of one or more microorganism/s in a biological sample, the kit comprising:
(a) an extraction solution comprising a quaternary ammonium compound including a silicon containing functional group; and
(b) at least one reagent for performing quantitative PCR.

According to a fifth aspect of the present invention, there is provided a kit for the detection and identification of one or more microorganism/s in a biological sample, the kit comprising:
(a) means for extracting DNA from the microorganism/s;
(b) at least one reagent for performing quantitative PCR; and
(c) one or more of the primer pair of SEQ ID NO. 1 and 2 together with the probe of SEQ ID NO. 7, and/or the primer pair of SEQ ID NO. 3 and 4 together with the probe of SEQ ID NO. 8.

According to a sixth aspect of the present invention, there is provided a kit for the detection and identification of one or more microorganism/s in a biological sample, the kit comprising:
(a) an extraction solution comprising a quaternary ammonium compound including a silicon containing functional group;
(b) at least one reagent for performing quantitative PCR; and
(c) one or more of the primer pair of SEQ ID NO. 1 and 2 together with the probe of SEQ ID NO. 7, and/or the primer pair of SEQ ID NO. 3 and 4 together with the probe of SEQ ID NO. 8.

According to a seventh aspect of the present invention there is provided a kit for the detection and identification of one or more microorganism/s in a biological sample, the kit comprising:
(a) means for extracting DNA from the microorganism/s;
(b) at least one reagent for performing PCR; and
(c) one or more of the primer pair of SEQ ID NO. 1 and 2 and/or the primer pair of SEQ ID NO. 3 and 4;
(d) means for visualising PCR products According to an eighth aspect of the present invention there is provided a pair of single stranded oligonucleotide primers and a probe for quantitative PCR detection of *Plasmodium* sp. DNA in a biological sample, the forward primer comprising the sequence identified in SEQ ID NO. 1, the reverse primer comprising the sequence identified in SEQ ID NO. 2 and the probe comprising the sequence identified in SEQ ID NO. 7.

According to a ninth aspect of the present invention there is provided a pair of single, stranded oligonucleotide primers and a probe for quantitative PCR detection of *Escherichia coli* DNA in a biological sample, the forward primer comprising the sequence identified in SEQ ID NO. 3, reverse primer comprising the sequence identified in SEQ ID NO. 4 and the probe comprising the sequence identified in SEQ ID NO. 8.

According to a tenth aspect of the present invention there is provided a pair of single stranded oligonucleotide primers and a probe for quantitative PCR detection of human DNA in a biological sample, the forward primer comprising the sequence identified in SEQ ID NO. 5, the reverse primer comprising the sequence identified in SEQ ID NO. 6, and the probe comprising the sequence identified in SEQ ID NO. 9.

According to an eleventh aspect of the present invention there is provided a set of single stranded oligonucleotide primers and probes for detection of one or more microorganism/s in a biological sample comprising the pairs of primers and associated probes according to the eighth and ninth, the eighth and tenth, the ninth and tenth, or the eighth, ninth and tenth aspects of the present invention.

According to a twelfth aspect of the present invention there is provided a use of a set of single stranded oligonucleotide primers and probes comprising the pair of primers and associated probe according to the eighth and ninth, the eighth and tenth, the ninth and tenth, or the eighth, ninth and tenth aspects of the present invention for quantitative PCR detection of one or more microorganism/s in a biological sample.

According to a thirteenth aspect of the present invention there is provided a use of the kit of the fourth, fifth, sixth or seventh aspects of the present invention for the detection and identification of one or more microorganism/s in a biological sample.

The preferred features of the fourth, fifth, sixth, seventh, eighth, ninth, tenth, eleventh, twelfth and thirteenth aspects are as defined hereinabove in relation to the first, second and third aspects.

In particular, means for extracting DNA are described hereinabove in relation to step (a) of the methods of the invention in which extraction of DNA is described. Means for visualising PCR products are described hereinabove in relation to step (c) of the method of the third aspect of the invention where visualisation of the PCR products is described.

The present invention will now be further described with reference to the following non-limiting examples and figures in which.

EXAMPLES

The following examples demonstrate the amplification and identification of microorganism DNA extracted from biological samples together with the use of a human gene control.

In each case, the extraction of DNA takes place by using the extraction solution described above. The supernatant isolated from the extraction is fully PCR compliant (either with end point or real time-qPCR-) and was used directly in the PCR methods described below.

Figure 1:
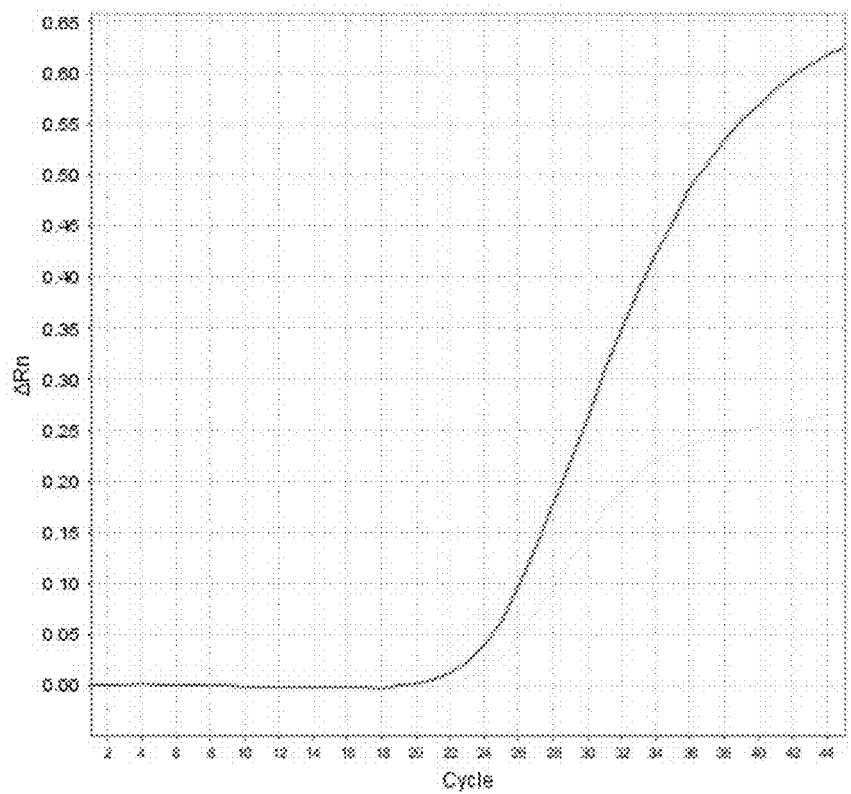
FIG. 1 shows the quantitative PCR results from a clinical blood sample indicating the presence of Protozoan *Plasmodium* sp. DNA.

Example I Detection and Identification of Protozoan *Plasmodium* sp. DNA Through gPCR FIG. 1 provided for this example was obtained by qPCR using the TaqMan® Universal PCR Master Mix (Applied Biosystems), containing HotStar Taq DNA polymerase, MgCl2 and dNTP's. *Plasmodium* sp. detection and identification required the use of the following oligonucleotide primers for protozoan target amplification during qPCR:

```
Primer Protozoan Forward:
                           (SEQ ID NO. 1)
5'-GTTAAGGGAGTGAAGACGATCAGA-3'

Primer Protozoan Reverse:
                           (SEQ ID NO. 2)
5'AACCCAAAGACTTTGATTTCTCATAA-3'
```

Plus the following probe for real time amplification on any qPCR system:

```
Probe Plasmodium:
                           (SEQ ID NO. 7)
5'-FAM-ACCGTCGTAATCTTAACCATAAACTATGCCGACTAG-

TAMRA-3'
```

The protozoan detection and identification described here in combination with the extraction step complies with the use of any standard PCR mastermix. Using the TaqMan® Universal PCR Master Mix (Applied Biosystems), the following mix was used for the generation of this example:

| | |
|---|---|
| PCR Master Mix: 12.5 µl | |
| Primer Protozoan F: 0.25 µl | |
| Primer Protozoan R: 0.25 µl | Mixture volume: 20 µl |
| *Plasmodium* sp. probe: 1.25 µl | |
| H₂O: 5.5 µl | |

Likewise, the following qPCR conditions were set:

| | | |
|---|---|---|
| Mix activation | 50° C. 2 min | |
| Initial denaturation | 95° C. 10 min | |
| Denaturation | 95° C. 15 sec | |
| | | 45 cycles |
| Annealing | 60° C. 60 sec | |

FIG. 1 shows the increased fluorescence of the *Plasmodium* probe during qPCR with the extracted DNA from the sample. Thereby indicating the presence of *Plasmodium* in the blood sample.

Example II Detection and Identification of Human Control DNA Through gPCR

Figure 2:
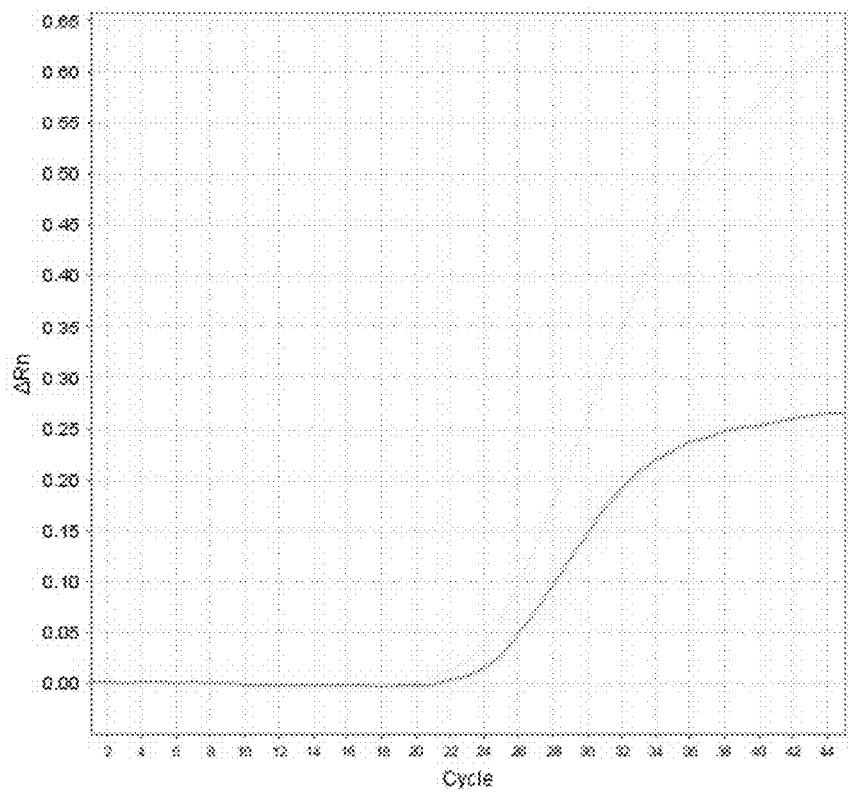
FIG. 2 shows the quantitative PCR results from a clinical blood sample indicating the presence of human RNAse-P DNA (internal control for the process of extraction and subsequent amplification for detection)

FIG. 2 provided for this example was obtained using the TaqMan® Universal PCR Master Mix (Applied Biosystems), containing HotStar Taq DNA polymerase, MgCl2 and dNTP's.

Human RNAse-P detection and identification requires the use of the following oligonucleotide primers for human target amplification:

```
Control Primer Forward:
                           (SEQ ID NO. 5)
5'-AGA TTTGGACCTGCGAGCG-3'

Control Primer Reverse:
                           (SEQ ID NO. 6)
5'-GAGCGGCTGTCTCCACAAGT-3'
```

Plus the following probe for real time amplification on any qPCR system:

```
Probe Human:
                           (SEQ ID NO. 9)
5'-FAM/VIC-TTCTGACCTGAAGGCTCTGCGCG-BHQ1-3'
```

The human RNAse-P detection and identification described here in combination with the extraction step complies with the use of any standard PCR mastermix. Using the TaqMan® Universal PCR Master Mix (Applied Biosystems), the following mix was used for the generation of this example:

| | |
|---|---|
| PCR Master Mix: 12.5 µl | |
| Control Primer F: 0.5 µl | |
| Control Primer R: 0.5 µl | Mixture volume: 20 µl |
| Human Probe: 0.5 µl | |
| H₂O: 6.0 µl | |

Likewise, the following qPCR conditions were set:

| | | |
|---|---|---|
| Mix activation | 50° C. 2 min | |
| Initial denaturation | 95° C. 10 min | |
| Denaturation | 95° C. 15 sec | |
| | | 45 cycles |
| Annealing | 60° C. 60 sec | |

FIG. 2 shows the increased fluorescence of the Human probe during qPCR with the extracted DNA from the sample. Thereby indicating the presence of human RNAse P DNA in the blood sample. This verifies that the sample is human and that the qPCR system is working correctly.

Example III Detection and Identification of Bacterial *E. coli* DNA Through End Point PCR This example uses the same components and set up as required for detection of bacterial targets through qPCR, but products resulting from amplification the extracted DNA by PCR were visualised on agarose gel to show compliance with end point PCR detection. This example used a qPCR approach to generate products of amplification that were fit for end point analysis on agarose gel.

Figure 3:
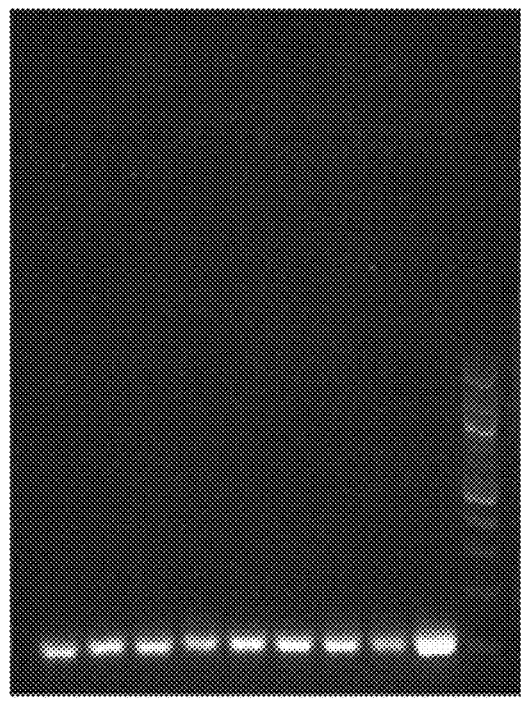
FIG. 3 shows the quantitative PCR results from a clinical blood sample indicating the presence of bacterial *E. coli* DNA.

FIG. 3 provided for this example was obtained using Promega® Universal PCR Master Mix, REF M7502. DNA polymerase, MgCl2 and dNTP's are contained premixed. Detection and identification of *E. coli* DNA requires the use of the following oligonucleotide primers for bacterial target amplification:

```
Bacterial Primer F:
                                (SEQ ID NO. 3)
EcoF 5'-GGAACTGGTGCCGGAACGC-3'

Bacterial Primer R:
                                (SEQ ID NO. 4)
5'-GACTTCGATCAGTTTGACG-3'
```

Plus the following probe for real time amplification on any qPCR* system:

```
Probe E. coli:
                                (SEQ ID NO. 8)
5'-FAM-CGTATCACTGCGCGCCACATTCG-TAMRA-3'
```

The *E. coli* detection and identification described here in combination with extraction step complies with the use of any standard PCR mastermix. Using the components described above, the following mix was used for the generation of this example (*the probe was not added, since it is necessary for qPCR detection and this example aimed to prove end point PCR compliance, making this element redundant) However, this component would be added as per examples 1 and 2 if real time qPCR were being conducted:

| | | |
|---|---|---|
| PCR Master Mix: 12.5 μl | | |
| Primers (each one): 0.5 μl | | Mixture volume: 20 μl |
| H₂O: 6.5 μl | | |

Likewise, the following qPCR conditions were set:

| | | |
|---|---|---|
| Initial denaturation | 94° C. 5 min | |
| Denaturation | 94° C. 20 sec | |
| Annealing | 54° C. 20 sec | 30 cycles |
| Extension | 72° C. 30 sec | |
| Final extension | 72° C. 5 min | |
| Cooling | 10° C. ∞ | |

FIG. 3 shows an agarose gel obtained from a 1% dilution of low electro-endosmosis agarose in TAE buffer as is known in the art. The gel was subjected to the classical electrophoresis field to separate the PCR products into size order, the PCR products are then visualised under a UV light. PCR products corresponding to amplification of the *E. coli* target are shown at the bottom of all lanes except the last lane on the left next to the molecular weight marker. This lane corresponds to amplification of the same target from the same blood sample subjected to a full Qiagen® purification process as positive control.

Figure 4:
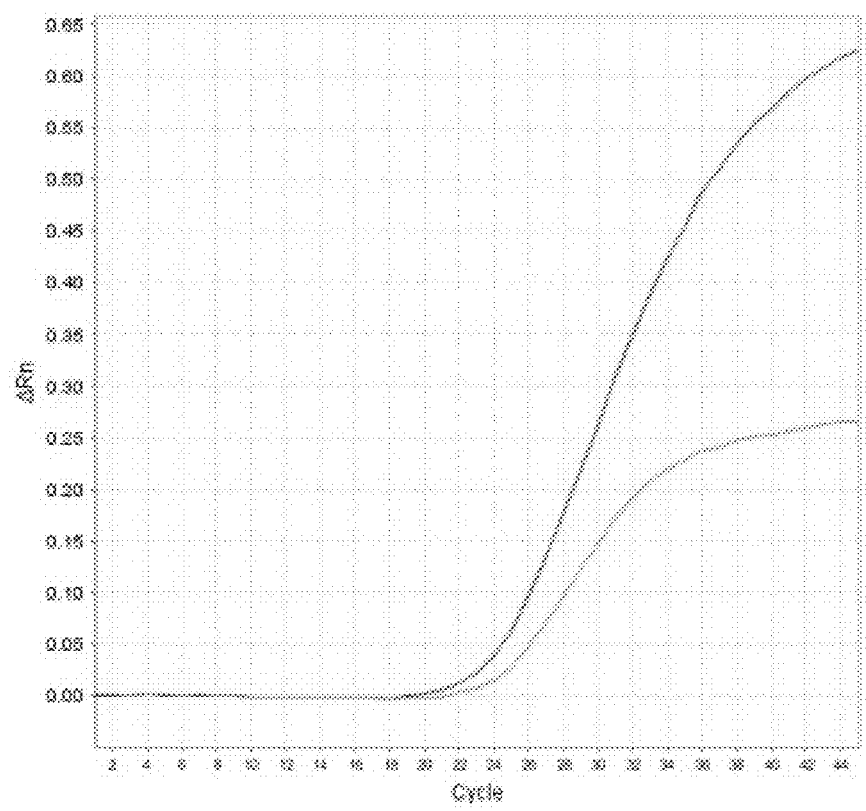
FIG. 4 shows the quantitative PCR results from a clinical blood sample indicating the combined presence of the human RNAse-P control DNA and Protozoan *plasmodium* sp. DNA

Example IV Parallel Detection and Identification of Human Control DNA and Protozoan *Plasmodium* sp. DNA Through qPCR FIG. 4 provided for this example was obtained using the TaqMane Universal PCR Master Mix (Applied Biosystems), containing HotStar Taq DNA polymerase, MgCl2 and dNTP's.

Parallel detection and identification of human RNAse-P gene and *plasmodium* sp. targets requires the use of the following oligonucleotide primers for combined human control and protozoan target amplification:

```
Primer Protozoan Forward:
                                (SEQ ID NO. 1)
5'-GTTAAGGGAGTGAAGACGATCAGA-3'

Primer Protozoan Reverse:
                                (SEQ ID NO. 2)
5'AACCCAAAGACTTTGATTTCTCATAA-3'

Control Primer Forward:
                                (SEQ ID NO. 5)
5'-AGA TTTGGACCTGCGAGCG-3'

Control Primer Reverse:
                                (SEQ ID NO. 6)
5'-GAGCGGCTGTCTCCACAAGT-3'
```

Plus the following probes for real time amplification on any qPCR system:

```
Probe Plasmodium:
                                (SEQ ID NO. 7)
5'-FAM-ACCGTCGTAATCTTAACCATAAACTATGCCGACTAG-
TAMRA-3'

(SEQ ID NO. 9)
Probe Human:
5'-FAM/VIC-TTCTGACCTGAAGGCTCTGCGCG-BHQ1-3'
```

The combined human control and protozoan detection and identification described here in combination with the extraction step complies with the use of any standard PCR mastermix. Using the TaqMane Universal PCR Master Mix (Applied Biosystems), the following mix was used for the generation of this example:

| | | |
|---|---|---|
| PCR Master Mix: 12.5 μl | | |
| ControlPrimer F: 0.5 μl | | |
| Control Primer R: 0.5 μl | | |
| Probe human: 0.5 μl | | |
| Primer FProtozoa.: 0.25 μl | | Mixture volume: 20 μl |
| Primer RProtozoa.: 0.25 μl | | |
| probe *plasmodium*: 1.25 μl | | |
| H₂O: 4.25 μl | | |

Likewise, the following qPCR conditions were set:

| Mix activation | 50° C. 2 min | |
| Initial denaturation | 95° C. 10 min | |
| Denaturation | 95° C. 15 sec | 45 cycles |
| Annealing | 60° C. 60 sec | |

FIG. 4 shows the increased fluorescence of the Human and *plasmodium* sp. probes during qPCR with the extracted DNA from the sample. Thereby indicating the presence of human RNAse P DNA and *Plasmodium* DNA in the blood sample. This verifies that the sample is human and that the qPCR system is working correctly whilst also identifying the microorganism contained in the sample.

The invention claimed is:

1. A method of detection and identification of one or more microorganism/s in a biological sample comprising the following steps:

(a) extracting DNA from the microorganism/s by contacting the microorganism/s with an extraction solution comprising a compound of general formula (I):

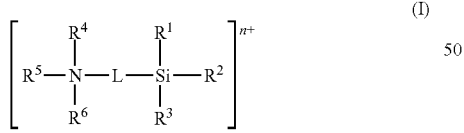

or a salt thereof wherein L is a linking group; each of $R^1$, $R^2$, $R^3$, $R^4$, $R^5$, and $R^6$ is independently selected from H, or an alkyl, alkenyl, aryl or alkoxy group, or an alkyl, alkenyl, aryl or alkoxy group substituted with one or more substituents selected from halo, hydroxy, nitro, mercapto amino, alkyl, alkoxy, phenol, sulfo, and sulfoxy; and n is 0 or 1; and (b) amplifying the extracted DNA and indicating the level of extracted DNA in a quantitative PCR;

wherein the quantitative PCR is performed using the primer pair of SEQ ID NO. 1 and 2 together with the probe of SEQ ID NO. 7; and wherein the method includes a step (a2) between step (a) and step (b) of contacting the material obtained in step (a) with a proteinaceous washing agent.

2. The method according to claim 1 wherein step (a) involves contacting the microorganism/s with a compound of formula (II):

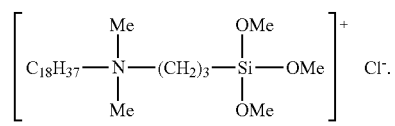

3. The method according to claim 1 wherein the extraction solution further comprises a solubilizing agent.

4. The method according to claim 3 wherein the solubilizing agent is an alkyl polyglucoside.

5. The method according to claim 1 wherein step (b) comprises the addition of at least one reagent for performing the quantitative PCR.

6. A method of detection and identification of one or more microorganism/s in a biological sample comprising the following steps:

(a) extracting DNA from the microorganism/s by contacting the microorganism/s with an extraction solution comprising a compound of general formula (I):

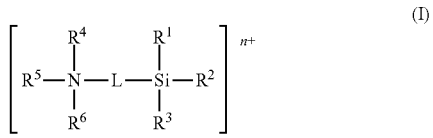

(I)

or a salt thereof wherein L is a linking group; each of $R^1$, $R^2$, $R^3$, $R^4$, $R^5$, and $R^6$ is independently selected from H, or an alkyl, alkenyl, aryl or alkoxy group, or an alkyl, alkenyl, aryl or alkoxy group substituted with one or more substituents selected from halo, hydroxy, nitro, mercapto amino, alkyl, alkoxy, phenol, sulfo, and sulfoxy; and n is 0 or 1;

(b) amplifying the extracted DNA in a PCR; and (c) visualizing the PCR products of step (b);

wherein the PCR in step (b) is performed using the primer pair of SEQ ID NO. 1 and 2; and wherein the method includes a step (a2) between step (a) and step (b) of contacting the material obtained in step (a) with a proteinaceous washing agent.

7. A kit for the detection and identification of one or more microorganism/s in a biological sample, the kit comprising:

(a) an extraction solution comprising a compound of general formula (I):

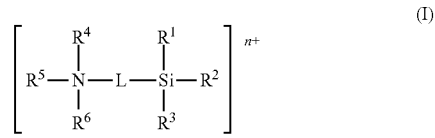

(I)

or a salt thereof wherein L is a linking group; each of $R^1$, $R^2$, $R^3$, $R^4$, $R^5$, and $R^6$ is independently selected from H, or an alkyl, alkenyl, aryl or alkoxy group, or an alkyl, alkenyl, aryl or alkoxy group substituted with one or more substituents selected from halo, hydroxy, nitro, mercapto amino, alkyl, alkoxy, phenol, sulfo, and sulfoxy; and n is 0 or 1; and (b) at least one reagent for performing quantitative PCR; and a proteinaceous washing agent; and (c) the primer pair of SEQ ID NO: 1 and 2 together with the probe of SEQ ID NO: 7.

8. The kit according to claim 7 which further comprises:

(d) means for visualizing PCR products.

9. The method according to claim 1 wherein the proteinaceous washing agent is selected from bovine serum albumin or acetylated bovine serum albumin.

10. The method according to claim 5, wherein the reagent for performing the quantitative PCR is selected from DNA polymerase, buffer, dNTPs, or a source of magnesium.

\* \* \* \* \*